(12) United States Patent
Cooreman et al.

(10) Patent No.: US 11,285,160 B2
(45) Date of Patent: Mar. 29, 2022

(54) PHARMACEUTICAL COMPOSITION AND METHOD FOR TREATMENT OF NON-ALCOHOLIC FATTY LIVER DISEASE

(71) Applicant: MITSUBISHI TANABE PHARMA CORPORATION, Osaka (JP)

(72) Inventors: Michael P. Cooreman, Randolph, NJ (US); Kohei Kikkawa, Osaka (JP)

(73) Assignee: MITSUBISHI TANABE PHARMA CORPORATION, Osaka (JP)

( * ) Notice: Subject to any disclaimer, the term of this patent is extended or adjusted under 35 U.S.C. 154(b) by 457 days.

(21) Appl. No.: 16/336,667

(22) PCT Filed: Sep. 26, 2017

(86) PCT No.: PCT/JP2017/034654
§ 371 (c)(1),
(2) Date: Mar. 26, 2019

(87) PCT Pub. No.: WO2018/062134
PCT Pub. Date: Apr. 5, 2018

(65) Prior Publication Data
US 2021/0290627 A1 Sep. 23, 2021

Related U.S. Application Data

(60) Provisional application No. 62/400,200, filed on Sep. 27, 2016.

(51) Int. Cl.
*A61K 31/538* (2006.01)
*A61K 45/06* (2006.01)

(52) U.S. Cl.
CPC ............ *A61K 31/538* (2013.01); *A61K 45/06* (2013.01)

(58) Field of Classification Search
CPC .................................................. A61K 31/538
See application file for complete search history.

(56) References Cited

U.S. PATENT DOCUMENTS

| | | | |
|---|---|---|---|
| 2009/0023716 A1 | 1/2009 | Iijima et al. | |
| 2011/0251185 A1 | 10/2011 | Iijima et al. | |
| 2015/0218113 A1 | 8/2015 | Okabe et al. | |
| 2016/0362385 A1 | 12/2016 | Okabe et al. | |

FOREIGN PATENT DOCUMENTS

| | | | | |
|---|---|---|---|---|
| EP | 2883870 | * | 6/2015 | ........... C07D 265/36 |
| EP | 2883870 A1 | | 6/2015 | |
| WO | WO 2007/089034 A1 | | 8/2007 | |
| WO | WO2007089034 | * | 8/2007 | ........... C07D 265/36 |
| WO | WO 2014/024950 A1 | | 2/2014 | |

OTHER PUBLICATIONS

Adorini et al., "Farnesoid X Receptor Targeting to Treat Nonalcoholic Steatohepatitis," Drug Discovery Today, vol. 17, Nos/17/18, Sep. 2012, pp. 988-997.
Browning et al., "Prevalence of Hepatic Steatosis in an Urban Population in the United States: Impact of Ethnicity," Hepatology, vol. 40, No. 6, Dec. 2004, pp. 1387-1395.
Chitturi et al., "Non-alcoholic Steatohepatitis in the Asia-Pacific Region:Future Shock?" Journal of Gastroenterology and Hepatology, vol. 19, 2004, pp. 368-374.
Day et al., "Who are the NAFLD Patients at Risk of Disease Progression?," EASL Postgraduate Course Metabolic Liver Disease, 50th International Liver Congress 2015, Apr. 22-23, 2015, pp. 93-98 (57 total pages).
Dyson et al., "Non-alcoholic Fatty Liver Disease: A Practical Approach to Treatment," Frontline Gastroenterology, http://fg.bmj.com/content/early/2014/01/22/flgastro-2013-100404, Published online Jan. 22, 2014, pp. 1-10 (11 total pages).
Eguchi et al., "Prevalence and Associated Metabolic Factors of Nonalcoholic Fatty Liver Disease in the General Population from 2009 to 2010 in Japan: A Multicenter Large Retrospective Study," J Gastroenterol, vol. 47, 2012 (Published online Feb. 11, 2012), pp. 586-595.
English translation of the International Search Report, dated Dec. 13, 2017, for International Application No. PCT/JP2017/034654.
International Preliminary Report on Patentability and English translation of the Written Opinion of the International Searching Authority, dated Apr. 2, 2019, for International Application No. PCT/JP2017/034654.

(Continued)

*Primary Examiner* — Paul V Ward
(74) *Attorney, Agent, or Firm* — Birch, Stewart, Kolasch & Birch, LLP

(57) ABSTRACT

The present invention provides a pharmaceutical composition for prophylaxis and treatment of NAFLD comprising as an active ingredient a 1,4-benzoxazine compound represented by formula (I): or a pharmaceutically acceptable salt thereof, and a pharmaceutically acceptable carrier, as well as a method for prophylaxis and treatment of NAFLD which comprises administering a therapeutically effective amount of the above-mentioned 1,4-benzoxazine compound represented by formula (I) and so on to a patient in need thereof.

(I)

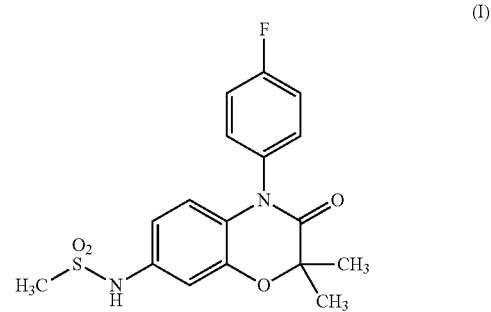

20 Claims, 2 Drawing Sheets

(56) References Cited

OTHER PUBLICATIONS

Kato et al., "Drug Metabolism—Basis for Clinical Pharmacy and Drug Development," The 3rd Edition, Japan, ISBN 978-4-8079-077-3, Jan. 15, 2010, pp. x-xi, 144-147, 150-151 and 250 (12 total pages).

Neuschwander-Tetri et al., "Farnesoid X Nuclear Receptor Ligand Obeticholic Acid for Non-cirrhotic, Non-alcoholic Steatohepatitis (FLINT): A Multicentre, Randomised, Placebo-controlled Trial," Lancet, vol. 385, Mar. 14, 2015 (Published online Nov. 7, 2014), pp. 956-965.

Noguchi et al., "Selective Aldosterone Blocker Ameliorates the Progression of Non-alcoholic Steatohepatitis in Rats," International Journal of Molecular Medicine, vol. 26, 2010, pp. 407-413.

Pfizer, "Eplerenone (SelaraTM) Tablet Pharmaceutical Interview Forms," Nov. 2015, pp. 1-75 (82 total pages).

Piotrowski, "Mineralocorticoid Receptor Antagonists for the Treatment of Hypertension and Diabetic Nephropathy," The Journal of Medical Chemistry, vol. 55, 2012 (Published Aug. 6, 2012), pp. 7957-7966, XP055213613.

Pizarro et al., "Beneficial Effects of Mineralocorticoid Receptor Blockade in Experimental Non-alcoholic Steatohepatitis," Liver International, vol. 35, No. 9, 2015 (Feb. 23, 2015), pp. 2129-2138, XP055431495.

Sass et al., "Nonalcoholic Fatty Liver Disease: A Clinical Review," Digestive Diseases and Sciences, vol. 50, No. 1, Jan. 2005, pp. 171-180.

Tamaki et al., "Angiotensin II Type 1 Receptor Antagonist Prevents Hepatic Carcinoma in Rats with Nonalcoholic Steatohepatitis," J Gastroenterol, vol. 48, 2013 (Published online Aug. 14, 2012), pp. 491-503.

Thomas et al., "Direct Transcriptional Regulation of Human Hepatic Cytochrome P450 3A4 (CYP3A4) by Peroxisome Proliferator-Activated Receptor Alpha (PPARα)," Molecular Pharmacology, vol. 83, Mar. 2013, pp. 709-718.

Williams et al., "Clinical Advances in Liver, Pancreas, and Biliary Tract, Prevalence of Nonalcoholic Fatty Liver Disease and Nonalcoholic Steatohepatitis Among a Largely Middle-Aged Population Utilizing Ultrasound and Liver Biopsy . . . ," Gastroenterology, vol. 140, Jan. 2011, pp. 124-131.

Yokohama et al., "Therapeutic Efficacy of an Angiotensin II Receptor Antagonist in Patients with Nonalcoholic Steatohepatitis," Hepatology, vol. 40, No. 5, 2004 (Published online Sep. 20, 2004), pp. 1222-1225.

\* cited by examiner

[Fig. 1]
Sirius red positive areas
Sirius Red (Collagen area)
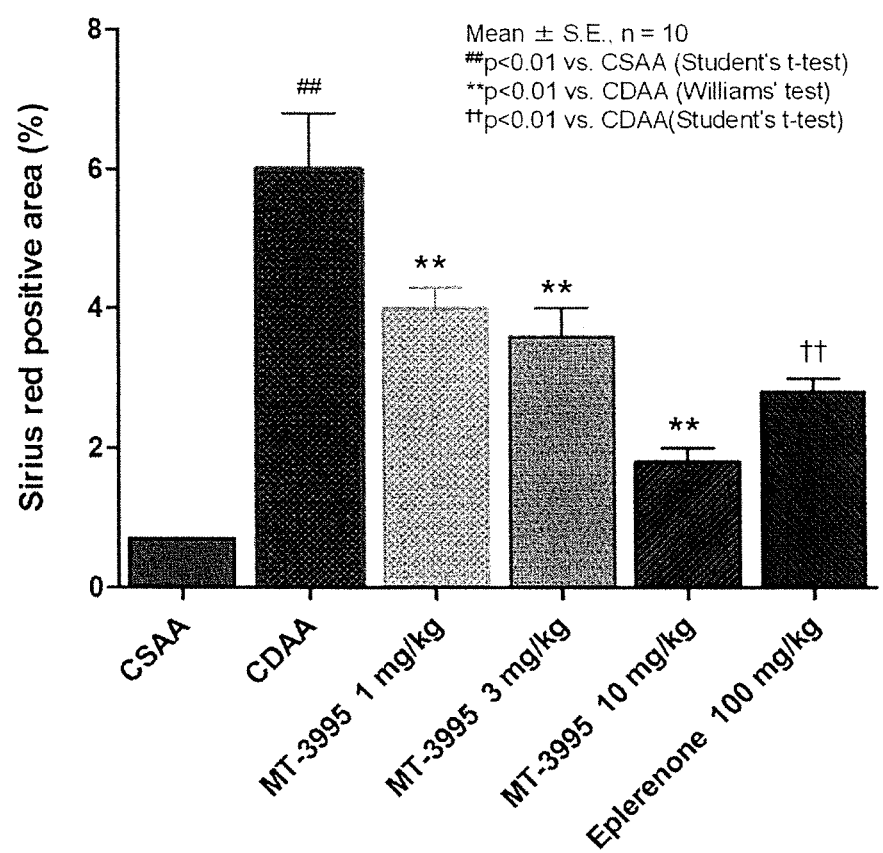

[Fig. 2]
Fibrosis development score
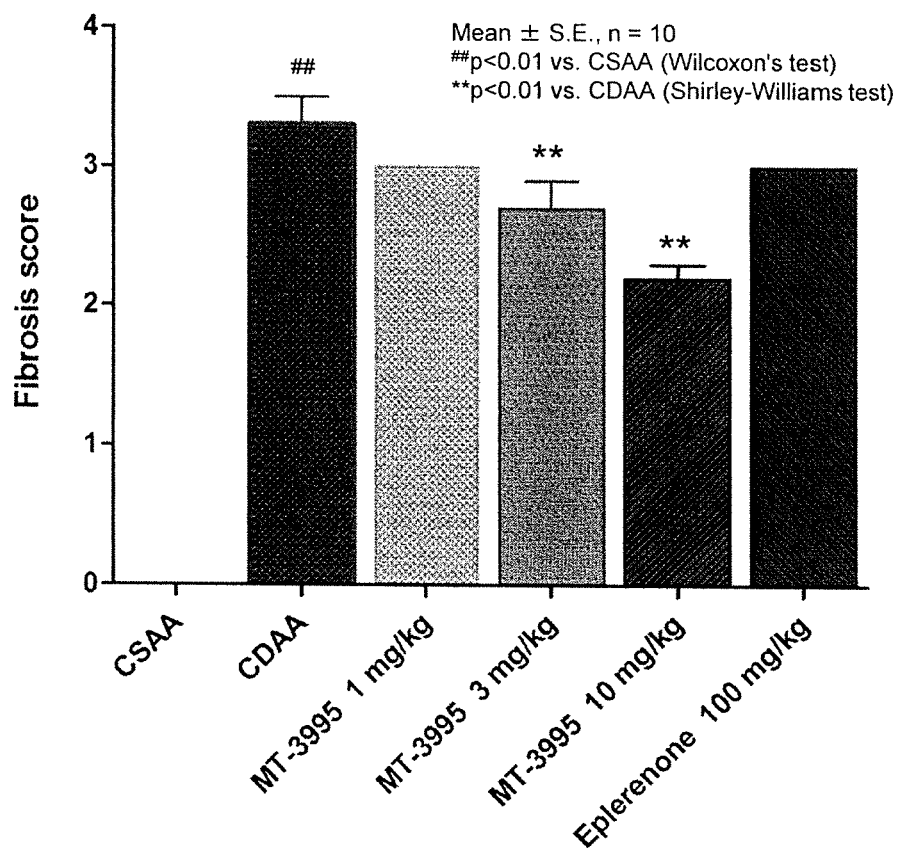

PHARMACEUTICAL COMPOSITION AND METHOD FOR TREATMENT OF NON-ALCOHOLIC FATTY LIVER DISEASE

TECHNICAL FIELD

The present invention relates to a novel pharmaceutical composition for prophylaxis and treatment of non-alcoholic fatty liver disease, and a novel method for prophylaxis and treatment of non-alcoholic fatty liver disease.

BACKGROUND ART

Non-alcoholic fatty liver disease (NAFLD) is a liver disease that is basically caused by insulin resistance, which is associated with obesity or lifestyle-related diseases, and encompasses a broad spectrum of liver diseases ranging from simple fatty liver to poor prognosis hepatic cirrhosis. Formerly, the fatty liver was thought to be a benign and non-progressive disease. However, after the establishment of the disease concept by Ludwig (1980), some evidence from non-clinical and clinical research has been accumulated, and as a result, it makes clear that there are some risks that NAFLD progresses non-alcoholic steatohepatitis (NASH) or hepatic cirrhosis, finally resulting in an onset of hepatocellular carcinoma (HCC). In many advanced countries, NAFLD is now the commonest cause of chronic liver disease, and accordingly, from the socioeconomic view, NAFLD is acknowledged as a disease on which there is the high necessity of interventions for the treatment at an earlier stage (see Non-Patent documents 1 and 2).

Many research reports on the prevalence of NAFLD have been known, and according to some of these reports, the prevalence of NAFLD in most advanced countries is estimated about 20 to 40% of a general population of a country (see Non-Patent documents 3 and 4), and 10 to 20% of NAFLD patients is estimated to be suffered from NASH (see Non-Patent documents 3 to 5). Also, according to another report, the prevalence of NAFLD for Japanese people is reported to be 29.7% (see Non-Patent document 6). Long-term follow-up studies in the past made it clear that a long-term prognosis of the NAFLD patient considerably depends on a stage of disease. For example, according to a long-term (until 15 years) follow-up study in the whole NAFLD patients as a target patient, it has been reported that the mortality of the patient was reached to 26%, which was 34 to 69% higher compared to a general population of the same age and sex. Also, according to the pooled data from the long-term (until 10 years) follow-up study in the NAFLD patients suffering from a high degree of fibrosis development and hepatic cirrhosis, the mortality of the patient was shown to be 16% (60% of which corresponds to liver-related death). While, according to the long-term (until 15 years) follow-up study in the NAFLD patients who do not suffer from a high degree of fibrosis development or hepatic cirrhosis, the liver-related mortality was shown to be up to about 9%. Further, another follow-up study is reported that the overall mortality or the liver-related mortality in the NAFLD patients who do not suffer from a high degree of fibrosis development or hepatic cirrhosis was not increased as compared to that of patients who observed with only fatty liver or that of patients who observed with only low degree of inflammation or cellular damage, but, in contrast, the NASH patients showed higher degree of the overall mortality or the liver-related mortality. The presence of hepatic fibrosis development and its severity observed by the liver biopsy has been thought to be an important factor for defining a long-term outcome of liver in NAFLD patient (see Non-Patent document 7).

The treatment for NAFLD/NASH is mainly focused on an improvement in lifestyle (for example, diet therapy and exercise therapy), and any evidence-based therapeutic agent has not been available yet, however, an effect of pioglitazone (insulin sensitizer) on hepatocellular damage and hepatic fibrosis development, or an effect of vitamin E on steatohepatitis has been reported (see Non-Patent document 1). As the other drugs whose possibility as a NASH therapeutic agent are under review, obeticholic acid, which is an agonist of a nuclear receptor for bile acids as a ligand (that is, Farnesoid X receptor), is known (see Non-Patent document 8). Also, with the respect to a drug that has an active site in Renin-Angiotensin System (RAS) (that is, applicability of angiotensin II type 1 receptor antagonist) to the NASH treatment has been reported (see Non-Patent documents 9 and 10). However, the correlation between RAS and an improvement effect on a condition of NASH is largely unknown. With respect to the correlation with RAS, selective aldosterone antagonist (SAB) has been reported to show an inhibitory effect on hepatic fibrosis development and so on in an animal model (see Non-Patent document 11) (in the document, the chemical structure of SAB that was used in the test is not specifically described).

Since eplerenone known as SAB has a short half-life in blood, and high doses are thus required to sustain the above-mentioned effect, it has been supposed that the risks of an onset of adverse effect associated with a high exposure in plasma (Cmax, AUC) (for example, an increased serum potassium level) are high, and an application of eplerenone for the treatment of NASH would be thus difficult. Also, since eplerenone is metabolized mainly by CYP3A4 (cytochrome P450 3A4), it has been reported that the risk of an onset of adverse effects are high in a patient population with hepatic impairment and an elderly patient population, whose drug metabolism activity of CYP3A4 is lowered (see Non-Patent document 12 and Non-Patent document 13 (pages 145 to 147, 150 to 151)). When eplerenone is administered with CYP3A4 inhibitor (the specific examples are as follows: diltiazem, verapamil, amlodipine, nifedipine, felodipine, atorvastatin, lovastatin, lomitapide, ticagrelor, cilostazol, ranolazine, amiodarone, dronedarone, fluoxetine, fluvoxamine, cimetidine or ranitidine), eplerenone is affected by a drug interaction with the CYP3A4 inhibitor, and a careful administration of eplerenone is thus required. In addition, since the patients who suffer from non-alcoholic fatty liver disease often have complications such as diabetes and hyperlipidemia, and multiple drugs are thus often used in combination, the drug with no concerns for the drug interaction has been requested as a therapeutic agent for nonalcoholic fatty liver disease.

Also, since NASH progresses due to combined factors such as fatty liver, inflammation and fibrosis development, it is predicted that a combination of multiple NASH therapeutic agents will be used in future. Obeticholic acid and elafibran or which are currently under clinical trial as a therapeutic agent for NASH are both thought to have an inductive effect on CYP3A4 from their mechanism of action (see Non-Patent documents 14 and 15), and when they are used in combination with eplerenone, a dose adjustment of eplerenone is thought to be required.

With respect to the compound (I) below-mentioned, though some documents discloses that the compound has an aldosterone antagonism (see Patent documents 1 and 2), there is no specific disclosure in the documents that the compound (I) inhibits a progression of hepatic fibrosis development and exerts a prophylactic or therapeutic effect on non-alcoholic fatty liver disease.

CITATION LIST

Patent Literature

PTL 1: WO 2007/089034 pamphlet
PTL 2: WO 2014/024950 pamphlet

Non Patent Literature

NPL 1: D. A. Sass et. al., Digestive Diseases and Sciences 2005; 50(1): 171-180
NPL 2: J. K. Dyson et. al., Frontline Gastroenterology, 2014; 0: 1-10
NPL 3: J. D. Browning et. al., Hepatology 2004; 40: 1387-1395
NPL 4: S. Chitturi et. al., J. Gastroenterol. Hepatol. 2004; 19: 368-374
NPL 5: C. D. Williams et. al., Gastroenterology 2011; 140: 124-131
NPL 6: Y. Eguchi et. al., Journal of Gastroenterology, 2012; 47: 586-595
NPL 7: C. Day et. al., The International Liver Congress 2015; EASL POSTGRADUATE COURSE METABOLIC LIVER DISEASE: 93-98
NPL 8: B. A. Neuschwander et. al., The Lancet 2015; 35: pp. 956-965
NPL 9: S. Yokohama et. al., Hapatology 2004; 40(5): 1222-1225
NPL 10: Y. Tamaki et. al., J. Gastroenterology 2013; 48: 491-503
NPL 11: R. Noguchi et. al., International Journal of Molecular Medicine 2010; 26: 407-413
NPL 12: Eplerenone (Selara™) Tablet Pharmaceutical Interview Forms
NPL 13: Drug Metabolism—Basis for Clinical Pharmacy and Drug Development, the 3rd edition, edited by R. Kato, T. Yokoi, and Y. Yamazoe
NPL 14: L. Adorini et. al., Drug Discovery Today 2012; 17: 988-997
NPL 15: M, Thomas et. al., Mol Pharmacol 2013; 83:709-718

SUMMARY OF INVENTION

Technical Problem

In the treatment of non-alcoholic fatty liver disease (NAFLD) including NASH, an effective drug treatment has not been established yet. Accordingly, an object of the present invention is to provide a novel and useful therapeutic agent and a method therefor.

Solution to Problem

The present invention provides a novel pharmaceutical composition for prophylaxis and treatment of Non-alcoholic fatty liver disease, and a novel method for prophylaxis and treatment of non-alcoholic fatty liver disease.

The present invention encompasses the following embodiments.

[Embodiment 1] A pharmaceutical composition for prophylaxis and treatment of non-alcoholic fatty liver disease (NAFLD), non-alcoholic simple fatty liver, nonalcoholic steatohepatitis (NASH), non-alcoholic hepatic fibrosis or non-alcoholic hepatic cirrhosis comprising as an active ingredient a 1,4-benzoxazine compound represented by formula (I):

[Chem. 1]

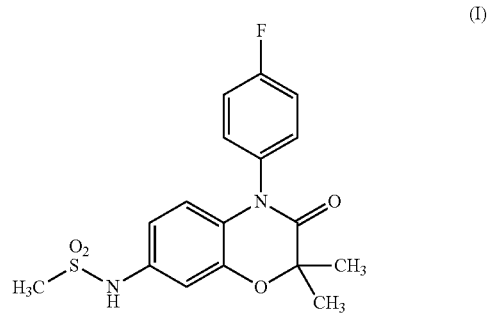

or a pharmaceutically acceptable salt thereof, and a pharmaceutically acceptable carrier.

[Embodiment 2] The pharmaceutical composition as described in [Embodiment 1] which is an agent for prophylaxis and treatment of non-alcoholic fatty liver disease (NAFLD).

[Embodiment 3] The pharmaceutical composition as described in [Embodiment 1] which is an agent for prophylaxis and treatment of non-alcoholic simple fatty liver.

[Embodiment 4] The pharmaceutical composition as described in [Embodiment 1] which is an agent for prophylaxis and treatment of non-alcoholic steatohepatitis (NASH).

[Embodiment 5] The pharmaceutical composition as described in [Embodiment 1] which is an agent for prophylaxis and treatment of non-alcoholic hepatic fibrosis.

[Embodiment 6] The pharmaceutical composition as described in [Embodiment 1] which is an agent for prophylaxis and treatment of non-alcoholic hepatic cirrhosis.

[Embodiment 7] The pharmaceutical composition as described in [Embodiment 1] for inhibition of a progression of non-alcoholic hepatic fibrosis development.

[Embodiment 8] The pharmaceutical composition as described in [Embodiment 1] for inhibition of a progression from non-alcoholic simple fatty liver to non-alcoholic steatohepatitis (NASH).

[Embodiment 9] The pharmaceutical composition as described in [Embodiment 1] for inhibition of a progression from non-alcoholic steatohepatitis (NASH) to non-alcoholic hepatic fibrosis.

[Embodiment 10] The pharmaceutical composition as described in [Embodiment 1] for inhibition of a progression from non-alcoholic hepatic fibrosis to non-alcoholic hepatic cirrhosis.

[Embodiment 11] The pharmaceutical composition as described in [Embodiment 1] for inhibition of a progression from non-alcoholic hepatic cirrhosis to liver cancer.

[Embodiment 12] The pharmaceutical composition as described in [Embodiment 1] for inhibition of a progression from non-alcoholic steatohepatitis (NASH) to liver cancer.

[Embodiment 13] The pharmaceutical composition as described in [Embodiment 1] wherein the pharmaceutical composition comprises as an active ingredient a daily dose of 1 to 25 mg of the compound (I) or a pharmaceutically acceptable salt thereof.

[Embodiment 14] The pharmaceutical composition as described in [Embodiment 13] wherein the pharmaceutical composition comprises as an active ingredient a daily dose of 1 to 10 mg of the compound (I) or a pharmaceutically acceptable salt thereof.

[Embodiment 15] The pharmaceutical composition as described in [Embodiment 14] wherein the pharmaceutical composition comprises as an active ingredient a daily dose of 2.5 to 10 mg of the compound (I) or a pharmaceutically acceptable salt thereof.

[Embodiment 16] The pharmaceutical composition as described in [Embodiment 15] wherein the pharmaceutical composition comprises as an active ingredient a daily dose of 2.5 mg, 5 mg, or 10 mg of the compound (I) or a pharmaceutically acceptable salt thereof.

[Embodiment 17] The pharmaceutical composition as described in [Embodiment 1] wherein the pharmaceutical composition is used in combination with one or more other therapeutic agents.

[Embodiment 18] The pharmaceutical composition as described in [Embodiment 17] wherein said other therapeutic agent is selected from the group consisting of at least one of angiotensin converting enzyme inhibitor, angiotensin II type 1 receptor antagonist, biguanide antidiabetic agent, thiazolidine antidiabetic agent, α-glucosidase inhibitor, insulin secretion promotors, vitamins, eicosapentaenoic acid, agents for treating dyslipidemia, HMG-CoA reductase inhibitor, ursodeoxycholic acid, and agents for treating non-alcoholic steatohepatitis (NASH).

[Embodiment 19] The pharmaceutical composition as described in [Embodiment 1] wherein at least one of said other therapeutic agent is selected from CYP3A4 inhibitor.

[Embodiment 20] The pharmaceutical composition as described in [Embodiment 19] wherein at least one of said other therapeutic agent is selected from the group consisting of diltiazem, verapamil, amlodipine, nifedipine, felodipine, atorvastatin, lovastatin, lomitapide, ticagrelor, cilostazol, ranolazine, amiodarone, dronedarone, fluoxetine, fluvoxamine, cimetidine and ranitidine.

[Embodiment 21] A method for prophylaxis and treatment of non-alcoholic fatty liver disease (NAFLD), non-alcoholic simple fatty liver, non-alcoholic steatohepatitis (NASH), non-alcoholic hepatic fibrosis or non-alcoholic hepatic cirrhosis which comprises administering a therapeutically effective amount of a 1,4-benzoxazine compound represented by formula (I):

[Chem. 2]

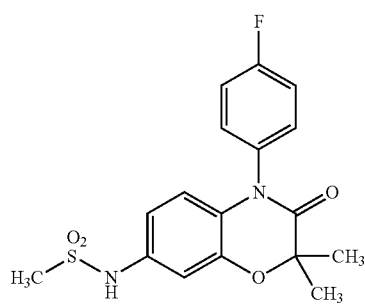

(I)

or a pharmaceutically acceptable salt thereof to a patient in need thereof.

[Embodiment 22] A use of a 1,4-benzoxazine compound represented by formula (I):

[Chem. 3]

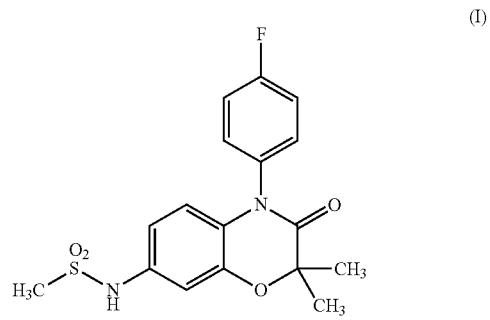

(I)

or a pharmaceutically acceptable salt thereof for the production of a pharmaceutical composition for prophylaxis and treatment of non-alcoholic fatty liver disease (NAFLD), non-alcoholic simple fatty liver, non-alcoholic steatohepatitis (NASH), non-alcoholic hepatic fibrosis or non-alcoholic hepatic cirrhosis.

Advantageous Effects of Invention

The pharmaceutical composition of the present invention is useful as an agent for prophylaxis and treatment of the above-mentioned non-alcoholic fatty liver disease.

BRIEF DESCRIPTION OF DRAWINGS

FIG. 1 represents a graph showing a test result of sirius red positive areas (as a primary endpoint) in CDAA diet-loaded rats.

FIG. 2 represents a graph showing a test result of fibrosis development score (as a secondary endpoint) in CDAA diet-loaded rats.

DESCRIPTION OF EMBODIMENTS

The term of "non-alcoholic fatty liver disease (NAFLD)" as used herein usually represents a disease state where a fat deposition to liver is recognized in a patient who does not have enough history of alcohol intake to evoke hepatic damages, and from which the cases where the disease causes is obvious, such as viral hepatitis and autoimmune hepatitis, is excluded.

The term of "non-alcoholic simple fatty liver" as used herein usually represents a disease state where only a fat deposition to hepatic cells is recognized.

The term of "non-alcoholic steatohepatitis (NASH)" as used herein usually represents a disease state where the similar observations to those found in alcoholic hepatitis (such as inflammation, hepatic cell necrosis, ballooning degeneration and/or fibrosis development) is associated with in addition to the above-mentioned fat deposition.

The term of "non-alcoholic hepatic fibrosis" as used herein usually represents a disease state where an overproduction and/or an accumulation of collagen is/are the other constitute components of extracellular matrix is/are recognized together with the progressed fibrosis development of the intrahepatic tissues.

The term of "non-alcoholic hepatic cirrhosis" as used herein usually represents a disease state where hepatic lobule structure is reconstructed due to a progressed fibrosis development.

The term of "prophylaxis and treatment of non-alcoholic fatty liver disease" as used herein includes an inhibition of a progression of non-alcoholic hepatic fibrosis development, an inhibition of a progression from non-alcoholic simple fatty liver to nonalcoholic steatohepatitis (NASH), an inhibition of a progression from the NASH to non-alcoholic hepatic fibrosis, an inhibition of a progression from the non-alcoholic hepatic fibrosis to non-alcoholic hepatic cirrhosis, and so on. Also the term of "prophylaxis and treatment of non-alcoholic fatty liver disease" in the present invention includes an inhibition of a progression from the non-alcoholic hepatic cirrhosis to liver cancer and an inhibition of a progression from the non-alcoholic steatohepatitis (NASH) to liver cancer.

The pharmaceutical composition of the present invention shows an excellent inhibitory effect on hepatic fibrosis development in NASH animal model (CDAA diet-loaded rat) as below-mentioned herein, and is thus useful as an agent for prophylaxis and treatment of non-alcoholic fatty liver disease.

For example, when steroidal aldosterone antagonist (such as Eplerenone) is used, severe adverse effects (such as gynecomastia, abnormality of menstruation, erectile dysfunction) is concerned.

Whereas, the pharmaceutical composition of the present invention has less concern about the above-mentioned severe adverse effects, and the pharmaceutical composition of the present invention is highly safe as pharmaceuticals.

The pharmaceutical composition of the present invention has pharmacokinetic characteristics of sustaining a certain plasma level for a prolonged time, and has thus long-sustaining effects for a prolonged time even at a lower dose, and further can be used with low toxicity and high safety.

It is estimated that the compound (I) as an active ingredient of the pharmaceutical composition of the present invention undergo glucuronide conjugation by UGT enzymes (Uridine diphosphate glucuronosyltransferase) as a main metabolic pathway, and thus the pharmaceutical composition of the present invention can be used in combination with a CYP3A4 inhibitor or a CYP3A4 inducer. Also, there is no UGT inhibitor showing so strong drug interactions that dose adjustment of compound (I) will be required on combination use. Thus the pharmaceutical composition of the present invention can be used in a patient suffering from non-alcoholic fatty liver disease with safety.

The term "compound (I)" as used herein is represented by formula (I):

[Chem. 4]

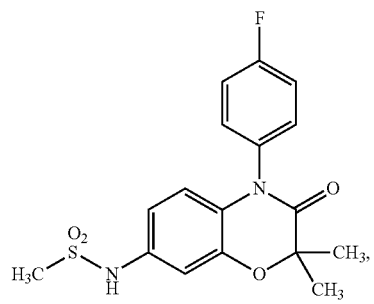

(I)

which has been known in WO 2007/089034 pamphlet.

The compound (I) can be clinically used either in the free form or in the form of a pharmaceutically acceptable salt thereof.

The term "pharmaceutically acceptable salt thereof" as used herein includes salts with an acid, including inorganic acid salts (such as a hydrochloride, a sulfate, a phosphate and a hydrobromide), and organic acid salts (such as an acetate, a fumarate, an oxalate, a citrate, a methanesulfonate, a bezenesulfonate, a tosylate, and a maleate); and salts with a base, including alkali metal salts (such as sodium salt and a potassium salt), and an alkaline-earth metal salts (such as calcium salt); and the others.

The compound (I) or a pharmaceutical acceptable salt thereof encompasses either intramolecular salts or additives thereof, and solvates or hydrates thereof. Also it has been known that a crystalline polymorphism of the compound (I) exists (see WO 2014/024950 pamphlet), and the active ingredient in the present invention (that is, compound (I)) can encompass any form of the crystalline polymorphism.

The pharmaceutical composition of the present invention can be administered orally or parenterally. Also the dosage form thereof is not specifically limited.

Examples of the term "pharmaceutical acceptable carrier" as used herein include excipients, binders, disintegrants, stabilizers. The compound (I) or a pharmaceutical acceptable salt thereof can be formulated with the pharmaceutical acceptable carrier to into the commonly-used dosage form (such as tablets, granules, capsules, powders, injections, inhalations, and suppositories).

The dose and frequency of administration of the pharmaceutical composition of the present invention may vary depending on the administration method, and the ages, body weights or disease conditions of the patients, and when orally administered, it is usually within a range of 1 to 25 mg/day, preferably within a range of 1 to 10 mg/day, and particularly preferably within a range of 2.5 to 10 mg/day.

The compound (I) or pharmaceutically acceptable salt thereof may be used singly or in combination with one or more other therapeutic agent(s) (the second active ingredient) depending on the diseases to be treated.

Examples of the therapeutic agent as the second active ingredient includes angiotensin converting enzyme inhibitor (such as enalapril maleate, imidapril hydrochloride), angiotensin II type 1 receptor antagonist (such as losartan, candesartan, telmisartan), biguanide antidiabetic agent (such as metformin), thiazolidine antidiabetic agent (such as pioglitazone hydrochloride), α-glucosidase inhibitor (such as voglibose), insulin secretion promotors (such as nateglinide), vitamins (such as vitamin E, vitamin C), eicosapentaenoic acid (EPA), agents for treating dyslipidemia (such as bezafibrate), HMG-CoA reductase inhibitor (such as pravastatin, atorvastatin), ursodeoxycholic acid (UDCA), and agents for treating NASH (such as obeticholic acid, Elafibranor) and the others.

When the compound (I) or pharmaceutically acceptable salt thereof is used in combination with other therapeutic agent (such as the above-mentioned second active ingredient), example of the administration form thereof includes (i) a formulation wherein the compound (I) and the other therapeutic agent are contained in the single administration form (combination drug), or (ii) the combined use of the formulation comprising the compound (I) and the formulation comprising the other therapeutic agent. Also, in the case of the above (ii), each of the administration route and/or the administration time of the respective used formulations may be the same or different.

The compound (I) that is used as an active ingredient in the present invention can be prepared, for example, according to a known method (for example, the methods described in the above-mentioned Patent Document 1 or 2).

EXAMPLES

Experiment 1
Method)

Some heads of F344 rats (5-week-old, body weight 67.5 to 87.5 g, purchased from Japan SLC, Inc.) were housed (for quarantine inspection and acclimatization) for 15 days while receiving a normal diet, and were then used as a test animal. The rats were divided into six treatment groups by stratified random allocation using body weight as a randomization factor (each 10 heads of the rats per group). The test compounds (that is, the compound (I) or eplerenone) were suspended into 0.5% aqueous carmellose sodium solution containing a vehicle (0.1% polyoxyethylene hydrogenated castor oil (HCO-60, manufactured by Nikko Chemicals Co., Ltd.)), and the resultant suspensions were used (10 mL/kg). The rats were loaded with a CDAA diet (choline deficient L-amino acid defined diet), and simultaneously with the loading, were received with a repeated oral administration of the above-mentioned compound (I) (1 mg/kg, 3 mg/kg, and 10 mg/kg) at once per day for 10 weeks (hereinafter, which is referred to as "Compound (I)-treated group"). Also, the rats that were loaded with the CDAA diet and were received with the administration of the above-mentioned vehicle (10 mL/kg) were assigned to "disease control group", and also the rats that were loaded with the CSAA diet and were received with the administration of the above-mentioned vehicle (10 mL/kg) were assigned to "normal control group". While, "positive control group" rats were loaded with the CDAA diet and were received with a repeated oral administration of eplerenone (100 mg/kg) at once per day for 10 weeks.

After the administration, the test tissues were sampled from lamella of the extracted liver, and the pathological specimens were constructed. Each effect of the respective test compound on NASH was examined using the Sirius red positive areas of the specimens as a primary endpoint. Also the fibrosis development scores of hepatic pathological specimens in each group were examined as the secondary endpoint.

Here, the test compound and the dose thereof in each group are listed in Table 1 below.

TABLE 1

| Group | Test compound and Dose | |
|---|---|---|
| Normal control group | No (vehicle) | |
| Disease control group | No (vehicle) | |
| Compound (I)-treated group | Compound (I) | 1 mg/kg |
| | | 3 mg/kg |
| | | 10 mg/kg |
| Positive control group | Eplerenone | 100 mg/kg |

Result)
1) Sirius Red Positive Areas (Primary Endpoint)

The Sirius red positive areas of each group are shown in Table 2 below and FIG. 1. The Sirius red positive areas of the disease control group were found to be significantly higher than those of the normal control group. All of the Sirius red positive areas of the compound (I)-treated groups (1 mg/kg-treated group, 3 mg/kg-treated group, and 10 mg/kg-treated group, respectively) were found to be significantly lower as compared with those of the disease control group. The compound (I) showed significantly lower area value even at the lowest dose in comparison with the case where eplerenone was used at a higher dose. Also the Sirius red positive areas of the normal control group were found to be significantly lower as compared with those of the disease control group.

Next, the dose (100 mg/kg) of eplerenone in this experiment is discussed below. If the above dose is extrapolated at the exposure level into human beings, the dose exceeds a limit dose at which a tolerability of a prolonged administration cannot be obtained due to an adverse effect such as hyperkalemia, and it is supposed that the dose of 100 mg/kg is difficult for an application to human beings (see non-patent document 12 (pages 10, 12, 24 and 25), and non-patent document 15 (page 25)).

TABLE 2

| Group | Sirius red positive areas (%) (mean ± S.E.) |
|---|---|
| Normal control group | 0.7 ± 0.0 |
| Disease control group | 6.0 ± 0.8 ## |
| Compound (I)-treated group | 4.0 ± 0.3 ** |
| | 3.6 ± 0.4 ** |
| | 1.8 ± 0.2 ** |
| Positive control group | 2.8 ± 0.2 †† |

$p < 0.01$ (vs Normal control group, Student's t-test)
** $p < 0.05$ (vs Disease control group, William's test)
†† $p < 0.01$ (vs Disease control group, Student's t-test)

2) Fibrosis Development Score (Secondary Endpoint)

The fibrosis development scores were determined by the standards as indicated in Table 3 below. The fibrosis development score of each group are showed in Table 4 and FIG. 2. The fibrosis development scores of the disease control group were found to be significantly higher value as compared with those of the normal control group. All of the fibrosis development scores of the compound (I)-treated groups (3 mg/kg-treated group and 10 mg/kg-treated group) were found to be significantly lower value as compared with those of the disease control group. While, the fibrosis development scores of the positive control (eplerenone-treated) group were found to be not significantly different from those of the disease control group.

TABLE 3

| Stage | Score |
|---|---|
| Non | 0 |
| Perisinusoidal or periportal | 1 |
| Perisinusoidal and portal/periportal | 2 |
| Bridging fibrosis | 3 |
| Hepatic cirrhosis | 4 |

TABLE 4

| Group | Fibrosis development score (mean ± S.E.) |
|---|---|
| Normal control group | 0.0 ± 0.0 |
| Disease control group | 3.3 ± 0.2 ## |
| Compound (I)-treated group | 3.0 ± 0.0 |
| | 2.7 ± 0.2 ** |
| | 2.2 ± 0.1 ** |
| Positive control group | 3.0 ± 0.0 |

$p < 0.01$ (vs Normal control group, Wilcoxon's test)
** $p < 0.01$ (vs Disease control group, Shirley-Williams' test)
Wilcoxon's test It is clear from the above test results that the compound (I) can significantly inhibit the progression of fibrosis development of liver in CDAA diet-loaded rats.

INDUSTRIAL APPLICABILITY

The present invention is useful as a therapeutic agent for prophylaxis and treatment of non-alcoholic fatty liver disease.

The invention claimed is:

1. A method for treatment of non-alcoholic fatty liver disease (NAFLD), non-alcoholic simple fatty liver, non-alcoholic steatohepatitis (NASH), non-alcoholic hepatic fibrosis or non-alcoholic hepatic cirrhosis which comprises administering a therapeutically effective amount of a 1,4-benzoxazine compound represented by formula (I):

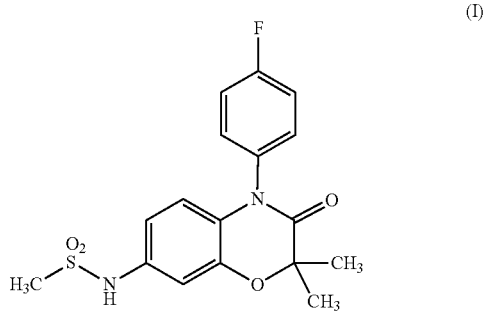

or a pharmaceutically acceptable salt thereof to a patient in need thereof.

2. The method according to claim 1 which is for treatment of non-alcoholic fatty liver disease (NAFLD).

3. The method according to claim 1 which is for treatment of non-alcoholic simple fatty liver.

4. The method according to claim 1 which is for treatment of non-alcoholic steatohepatitis (NASH).

5. The method according to claim 1 which is for treatment of non-alcoholic hepatic fibrosis.

6. The method according to claim 1 which is for treatment of non-alcoholic hepatic cirrhosis.

7. The method according to claim 1 for inhibition of a progression of non-alcoholic hepatic fibrosis development.

8. The method according to claim 1 for inhibition of a progression from non-alcoholic simple fatty liver to non-alcoholic steatohepatitis (NASH).

9. The method according to claim 1 for inhibition of a progression from non-alcoholic steatohepatitis (NASH) to non-alcoholic hepatic fibrosis.

10. The method according to claim 1 for inhibition of a progression from non-alcoholic hepatic fibrosis to non-alcoholic hepatic cirrhosis.

11. The method according to claim 1 for inhibition of a progression from non-alcoholic hepatic cirrhosis to liver cancer.

12. The method according to claim 1 for inhibition of a progression from non-alcoholic steatohepatitis (NASH) to liver cancer.

13. The method according to claim 1 wherein the compound (I) or a pharmaceutically acceptable salt thereof is administered as a daily dose of 1 to 25 mg.

14. The method according to claim 13 wherein the compound (I) or a pharmaceutically acceptable salt thereof is administered as a daily dose of 1 to 10 mg.

15. The method according to claim 14 wherein the compound (I) or a pharmaceutically acceptable salt thereof is administered as a daily dose of 2.5 to 10 mg.

16. The method according to claim 15 wherein the compound (I) or a pharmaceutically acceptable salt thereof is administered as a daily dose of 2.5 mg, 5 mg, or 10 mg.

17. The method according to claim 1 wherein the compound (I) or a pharmaceutically acceptable salt thereof is used in combination with one or more other therapeutic agents.

18. The method according to claim 17 wherein said other therapeutic agent is selected from the group consisting of at least one of angiotensin converting enzyme inhibitor, angiotensin II type 1 receptor antagonist, biguanide antidiabetic agent, thiazolidine antidiabetic agent, α-glucosidase inhibitor, insulin secretion promotors, vitamins, eicosapentaenoic acid, agents for treating dyslipidemia, HMG-CoA reductase inhibitor, ursodeoxycholic acid, and agents for treating non-alcoholic steatohepatitis (NASH).

19. The method according to claim 17 wherein at least one of said other therapeutic agent is selected from CYP3A4 inhibitor.

20. The method according to claim 19 wherein at least one of said other therapeutic agent is selected from the group consisting of diltiazem, verapamil, amlodipine, nifedipine, felodipine, atorvastatin, lovastatin, lomitapide, ticagrelor, cilostazol, ranolazine, amiodarone, dronedarone, fluoxetine, fluvoxamine, cimetidine and ranitidine.

* * * * *